(12) United States Patent
Miyashita et al.

(10) Patent No.: US 10,267,731 B2
(45) Date of Patent: Apr. 23, 2019

(54) FLUORESCENCE OBSERVATION METHOD

(71) Applicant: HAMAMATSU PHOTONICS K.K., Hamamatsu-shi, Shizuoka (JP)

(72) Inventors: Takayuki Miyashita, Hamamatsu (JP); Kanako Nakajima, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 16/017,242

(22) Filed: Jun. 25, 2018

(65) Prior Publication Data
US 2018/0306717 A1    Oct. 25, 2018

Related U.S. Application Data

(63) Continuation of application No. 15/507,772, filed as application No. PCT/JP2015/075104 on Sep. 3, 2015, now Pat. No. 10,031,079.

(30) Foreign Application Priority Data

Oct. 23, 2014  (JP) ................. 2014-216157

(51) Int. Cl.
*G01N 21/64*    (2006.01)
*A61B 5/00*    (2006.01)
*A61B 10/00*    (2006.01)
(Continued)

(52) U.S. Cl.
CPC ........... *G01N 21/64* (2013.01); *A61B 5/0071* (2013.01); *A61B 10/00* (2013.01); *C09K 11/00* (2013.01);
(Continued)

(58) Field of Classification Search
CPC ..... A61B 5/0059; A61B 5/0071; A61B 10/00; A61B 2576/00; C09K 11/00;
(Continued)

(56) References Cited

U.S. PATENT DOCUMENTS

2010/0245551 A1  9/2010  Morita
2011/0071403 A1  3/2011  Sevick-Muraca et al.

FOREIGN PATENT DOCUMENTS

JP   2006-340796 A   12/2006
JP   2009-226067 A   10/2009
(Continued)

OTHER PUBLICATIONS

English-language translation of International Preliminary Report on Patentability (IPRP) dated May 4, 2017 that issued in WO Patent Application No. PCT/JP2015/075104.
(Continued)

*Primary Examiner* — Mark R Gaworecki
(74) *Attorney, Agent, or Firm* — Drinker Biddle & Reath LLP

(57) ABSTRACT

This fluorescence observation method is a method of observing a living organism into which a fluorescent dye is injected. The method includes the steps of: irradiating the living organism with excitation light including a wavelength for exciting the fluorescent dye using a light irradiation means, acquiring a first fluorescence image of the living organism generated by the irradiation with the excitation light using an image acquisition means, specifying an observation object in the living organism on the basis of the first fluorescence image; acquiring a second fluorescence image of the observation object generated by the irradiation with the excitation light using the image acquisition means; and specifying a linear fluorescence pattern appearing in the second fluorescence image.

7 Claims, 5 Drawing Sheets

(51) Int. Cl.
    *C09K 11/00*    (2006.01)
    *G06T 7/00*     (2017.01)
    *G01N 21/39*    (2006.01)

(52) U.S. Cl.
    CPC .......... *G06T 7/0012* (2013.01); *A61B 5/0059* (2013.01); *A61B 2576/00* (2013.01); *C09K 2211/1037* (2013.01); *C09K 2211/1044* (2013.01); *G01N 2021/392* (2013.01); *G01N 2021/6417* (2013.01)

(58) Field of Classification Search
    CPC .... C09K 2211/1037; C09K 2211/1044; G01N 21/64; G01N 2021/392; G01N 2021/6417; G06T 7/0012
    See application file for complete search history.

(56) References Cited

FOREIGN PATENT DOCUMENTS

| | | |
|---|---|---|
| JP | 2013-003495 A | 1/2013 |
| JP | 5330510 B2 | 10/2013 |
| WO | WO-2010/137358 A1 | 12/2010 |
| WO | WO-2013/150745 A1 | 10/2013 |

OTHER PUBLICATIONS

Holly A. Robinson et al., "Non-invasive Optical Imaging of the Lymphatic Vasculature of a Mouse", Journal of Visualized Experiments, No. 73, Mar. 8, 2013, p. 2, XP055450231.

Peter Bankhead, "Analyzing Fluorescence microscopy images with ImageJ", Retrieved from the Internet: URL:https://blogs.qub.ac.uk/ccbg/files/2014/05/2014-05_Analyzing_fluorescence_microscopy_images.pdf, May 1, 2014, XP055450084.

JP Office Action dated Jun. 5, 2018 that issued in Japanese patent application No. P2014-216157 attached.

Rika Matsumoto et al., "Approach of Manual Lymph Drainage Guidance against Lymphedema"—Application of Fluorescent Contrast Radiography of Lymphatic Vessel to Patients after Breast Cancer Surgery—, The 37th Japanese Nursing Association Proceeding—Medical Surgical Nursing II—, Aug. 31, 2006, p. 289, including English translation.

Masaki Sano et al., "Observation in Change with Time in Rat Model with Lymphedema Using Fluorescent Imaging," The 35th Annual Meeting of the Japanese Society for Photomedicine and Photobiology, Jul. 2013, p. 42, including English translation.

Mitsunaga Narushima et al., "Identification of Lymphatic vessel in Limb Using ICG Fluorescence Method and Treatment of lymphedema," Journal of medical practice Surgery, Sep. 2009, pp. 934-938, vol. 71, No. 9, including English translation.

FLUORESCENCE OBSERVATION METHOD

TECHNICAL FIELD

The present invention relates to a fluorescence observation method and a fluorescence observation device.

BACKGROUND ART

In conventional lymphedema diagnosis, for example, scintigraphy is used, but there is a problem in that it is difficult to obtain local image information of an affected limb. Also, there is a problem in that an inspection is complex. On the other hand, a technique capable of observing a detailed state of lymphedema through fluorescence observation using a fluorescent dye such as indocyanine green in real time has recently been developed. In the fluorescence observation, observation of the fluorescence pattern is performed by irradiating an observation object with excitation light for exciting the fluorescent dye after the fluorescent dye is injected into the observation object.

As a fluorescence observation device used in the fluorescence observation, for example, there is a fluorescence observation device disclosed in Patent Literature 1. This fluorescence observation device is configured to include a light source which generates excitation light, an acquisition unit which acquires fluorescence information generated from an observation object by irradiation with the excitation light, an acquisition unit which acquires fluorescence information generated from a residue of the observation object by irradiation with the excitation light, and a correction unit which corrects fluorescence information so that fluorescence from the residue is suppressed.

CITATION LIST

Patent Literature

[Patent Literature 1] Japanese Unexamined Patent Publication No. 2009-226067

SUMMARY OF INVENTION

Technical Problem

As a type of treatment of lymphedema, for example, treatment (lymph drainage) of massaging the vicinity of the lymphedema and guiding stagnant lymph in a lymphedema portion into the normal lymphatic system is performed. In order to effectively perform the lymph drainage, it is important to precisely recognize a lymphatic drainage path through which the lymph fluid is drained from the portion in which the lymphedema occurs to the normal lymphatic system.

The present invention has been made to solve the above-described problem, and an objective of the invention is to provide a fluorescence observation method and a fluorescence observation device capable of precisely recognizing a lymphatic drainage path from a portion in which lymphedema occurs to the normal lymphatic system.

Solution to Problem

A fluorescence observation method according to an aspect for solving the above-described problem is a method of observing a living organism into which a fluorescent dye is injected, the method including the steps of: irradiating the living organism with excitation light including a wavelength for exciting the fluorescent dye using a light irradiation means; acquiring a first fluorescence image of the living organism generated by the irradiation with the excitation light using an image acquisition means; specifying an observation object in the living organism on the basis of the first fluorescence image; acquiring a second fluorescence image of the observation object generated by the irradiation with the excitation light using the image acquisition means; and specifying a linear fluorescence pattern appearing in the second fluorescence image.

In the fluorescence observation method, first, a region including a lymphedema portion is specified as an observation region on the basis of the first fluorescence image obtained by irradiating the living organism into which the fluorescent dye is injected with the excitation light. Therefore, the linear fluorescence pattern appearing in the second fluorescence image obtained by irradiating the observation object with the excitation light is specified. The linear fluorescence pattern is a fluorescence pattern indicating a lymphatic drainage path for draining lymph from a portion in which lymphedema occurs to the normal lymphatic system. Therefore, it is possible to precisely recognize the lymphatic drainage path by specifying the linear fluorescence pattern.

Also, the second fluorescence image may be an image acquired when one minute or more has elapsed from the injection of the fluorescent dye into the living organism. In this case, it possible to recognize the lymphatic drainage path more precisely by observing the linear fluorescence pattern in the second fluorescence image.

Also, fluorescent light from the living organism and a part of background light may be input to the image acquisition means using a light control means. In this case, it is possible to acquire an image of fluorescence including an image of an indicator material such as a finger or a pen together. The lymphatic drainage path is easily recognized on the basis of the specification of the linear fluorescence pattern when the indicator material is designated as a reference.

Also, the method may further include the step of: adjusting luminance of an image of fluorescence based on the fluorescent light from the observation object and an image of a background based on the part of the background light using an image processing means. In this case, the luminance of the linear fluorescence pattern in the fluorescence image is emphasized and the recognition of the lymphatic drainage path is further facilitated.

Also, a massage method according to an aspect includes the steps of specifying a linear fluorescence pattern according to the above-described fluorescence observation method and massaging the living organism on the basis of the specified linear fluorescence pattern.

The linear fluorescence pattern is a fluorescence pattern indicating a lymphatic drainage path for draining lymph from a portion in which lymphedema occurs to the normal lymphatic system. Therefore, it is possible to efficiently drain lymph from the portion in which lymphedema, occurs to the normal lymphatic system by performing the massage for the lymphatic drainage path.

Also, a fluorescence observation device according to an aspect is a device for observing a living organism into which a fluorescent dye is injected, the device including: a light irradiation means for irradiating the living organism with excitation light including a wavelength for exciting the fluorescent dye; an image acquisition means for acquiring a fluorescence image of the living organism generated by the irradiation with the excitation light; and an analysis means for specifying an observation object in the living organism on the basis of the fluorescence image and specifying a linear fluorescence pattern appearing in the fluorescence image of the observation object.

In the fluorescence observation device, an observation region is specified on the basis of the fluorescence image obtained by irradiating the living organism into which the fluorescent dye is injected with the excitation light and the linear fluorescence pattern appearing in the fluorescence image obtained by irradiating the observation object with the excitation light is specified. The linear fluorescence pattern is a fluorescence pattern indicating a lymphatic drainage path for draining lymph from a portion in which lymphedema occurs to the normal lymphatic system. Therefore, it is possible to precisely recognize the lymphatic drainage path by specifying the linear fluorescence pattern.

Also, the fluorescence image of the observation object may be an image acquired when one minute or more has elapsed from the injection of the fluorescent dye into the living organism. In this case, it possible to recognize the lymphatic drainage path more precisely by observing the linear fluorescence pattern in the fluorescence image.

Also, the device may further include a light control means for inputting fluorescent light from the observation object and a part of background light to the image acquisition means. In this case, it is possible to obtain an image of fluorescence including an image of an indicator material such as a finger or a pen together. The lymphatic drainage path is easily recognized on the basis of the specification of the linear fluorescence pattern by designating the indicator material as a basis.

Also, the device may further include an image processing means for adjusting luminance of an image of fluorescence based on the fluorescent light and an image of a background based on the part of the background light. In this case, the luminance of the linear fluorescence pattern in the fluorescence image is emphasized and the recognition of the lymphatic drainage path is further facilitated.

Advantageous Effects of Invention

According to an aspect of the present invention, it is possible to precisely recognize a lymphatic drainage path from a portion in which lymphedema occurs to the normal lymphatic system.

DESCRIPTION OF EMBODIMENTS

Hereinafter, details of preferred embodiments of a fluorescence observation method and a fluorescence observation device according to the present invention will be described with reference to the drawings.

Figure 1:
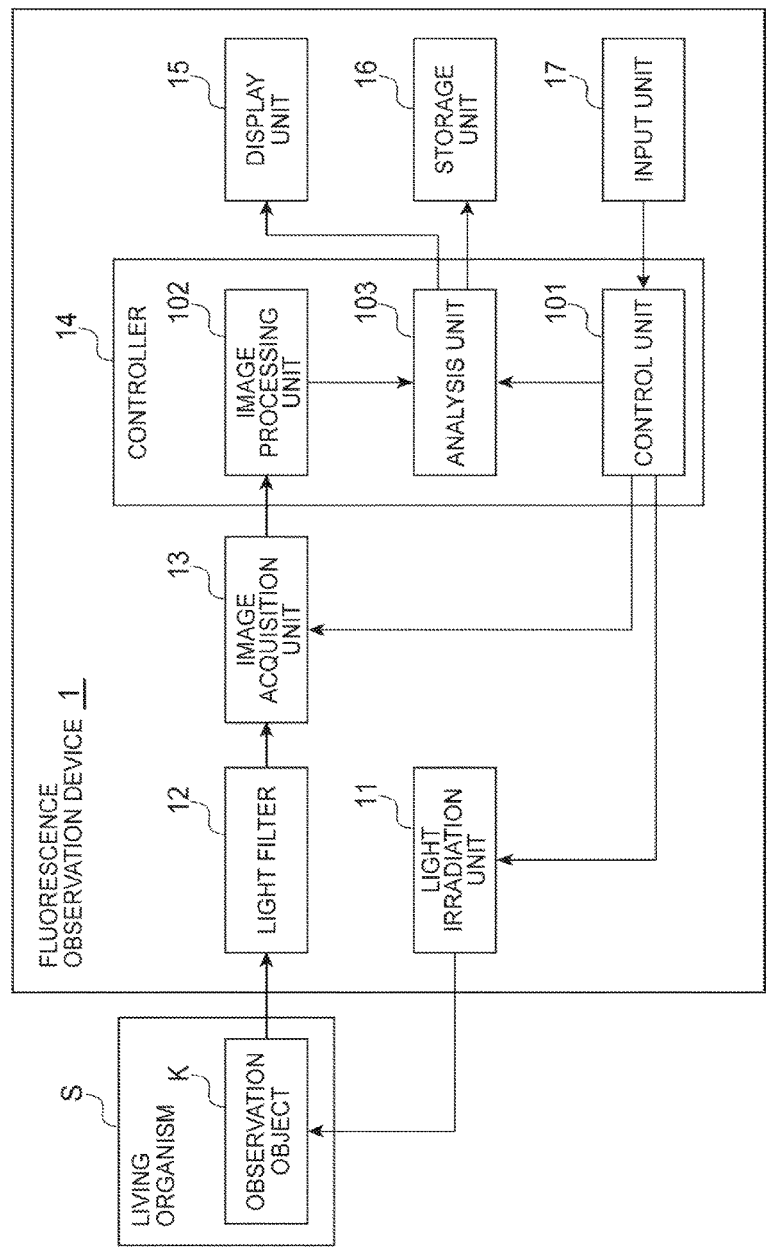
FIG. 1 is a block diagram illustrating an embodiment of a fluorescence observation device according to the present invention.

FIG. 1 is a block diagram illustrating an embodiment of a fluorescence observation device according to the present invention. The fluorescence observation device 1 illustrated in FIG. 1 is a device which observes a state of lymphedema according to fluorescence observation using a fluorescent dye. An observation object K of the fluorescence observation device 1 is a portion in which lymphedema occurs, i.e., a portion in which a flow of lymph is stagnant in the lymphatic system of a living organism S. For example, indocyanine green is used as the fluorescent dye. The indocyanine green is excited by infrared light and emits light of infrared fluorescence having a wavelength different from that of the excitation light. Because both the excitation light and the light of infrared fluorescence are easily transmitted through the living organism S, they are appropriate for fluorescence observation of a deep portion of the living organism S. An example of another fluorescent dye is methylene blue.

The fluorescence observation device 1 is configured to include a light irradiation unit (a light irradiation means) 11, a light filter (a light control means) 12, an image acquisition unit (an image acquisition means) 13, and a controller 14. The light irradiation unit 11 includes a light source which outputs light (excitation light) including a wavelength for exciting the fluorescent dye. Also, the light irradiation unit 11 includes an optical system which irradiates the living organism S and the observation object K which is a part of the living organism S with light from the light source. An example of the light source includes a laser light source such as a laser diode, an LED, an SLD, and a lamp light source. The light irradiation unit 11 may include a single light source or a plurality of light sources.

Figure 2:
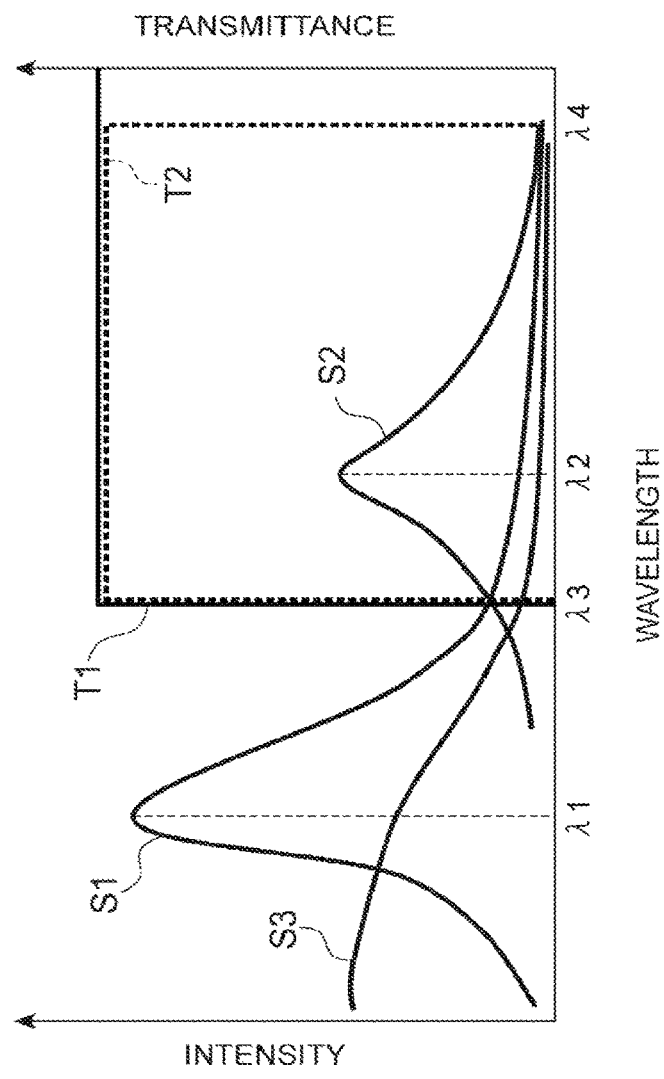
FIG. 2 is a diagram illustrating an example of characteristics of a light filter.

The light filter 12 is an optical element which adjusts a wavelength of light incident on the image acquisition unit 13 and is arranged between the living organism S and the observation object K which is a part of the living organism S and the image acquisition unit 13. FIG. 2 is a diagram illustrating an example of characteristics of the light filter. In FIG. 2, a spectrum S1 of excitation light output from the light irradiation unit 11, a spectrum S2 of fluorescent light generated in the observation object K by the irradiation with the excitation light, a spectrum S3 of background light around the living organism S and the observation object K, a transmission spectrum T1 when a long-pass filter is used as the light filter 12, and a transmission spectrum T2 when a band-pass filter is used as the light filter 12 are illustrated. Only the long-pass filter or the band-pass filter may be used as the light filter 12. Also, a combination of these filters may be used. The background light is, for example, light output from a fluorescent lamp arranged within an observation chamber.

If the indocyanine green is used as the fluorescent dye, a peak wavelength $\lambda 1$ of the spectrum S1 of the excitation light is, for example, about 760 nm. Also, the wavelength band of the spectrum S2 of the fluorescent light is about 760 nm to 1000 nm and a peak wavelength $\lambda 2$ is about 850 nm. Also, the spectrum S3 of the background light mainly has a peak in a visible band and is normally gradually reduced at an intensity which is less than that of the spectrum S2 of the fluorescent light at an infrared side.

If the long-pass filter is used as the light filter 12 with respect to the spectra S1 to S3, light of a wavelength greater than the wavelength λ3 between the peak wavelength λ1 and the peak wavelength λ2 is transmitted through the light filter 12. On the other hand, if the band-pass filter is used as the light filter 12, light of a wavelength band which is greater than a wavelength λ3 between the peak wavelength λ1 and the peak wavelength λ2 and is less than a wavelength λ4 of an edge on a long-wavelength side of the spectrum S2 of the fluorescent light is transmitted through the light filter 12. Therefore, regardless of whether the long-pass filter or the band-pass filter is used, the excitation light is shielded and the fluorescent light and a part of the background light are transmitted in the light filter 12.

The image acquisition unit 13 includes a light detector for acquiring a fluorescence image of the living organism S and the observation object K generated by the irradiation with the excitation light. For example, an area image sensor such as a CCD image sensor or a CMOS image sensor or a point sensor such as a photodiode or a photomultiplier tube is used as the light detector. The image acquisition unit 13 receives fluorescent light transmitted through the light filter 12 and acquires the fluorescence image of the living organism S and the observation object K. The image acquisition unit 13 outputs fluorescence image data including an image of fluorescence and an image of a background to the controller 14. The image acquisition unit 13 may acquire the fluorescence image of the living organism S or the observation object K as moving-image data or sill-image data.

The controller 14 is a computer system physically including a CPU, a memory, a communication interface, etc. or a hardware system constituted of a field-programmable gate array (FPGA) or a digital circuit. As illustrated in FIG. 1, the controller 14 is connected to a display unit 15 such as a display, a storage unit 16 such as a hard disk, and an input unit 17 such as a keyboard or a mouse. This controller 14 includes a control unit (a control circuit) 101, an image processing unit (an image processing means or an image processing circuit) 102, and an analysis unit (an analysis means or an analysis processing circuit) 103 as functional components.

The control unit 101 includes a control circuit which controls the light irradiation unit 11, the image acquisition unit 13, and the analysis unit 103. The control unit 101 receives an instruction of an output start of the excitation light by the light irradiation unit 11, an input of an image acquisition condition such as a frame rate or a contrast, or the like from the input unit 17 and controls operations of the light irradiation unit 11 and the image acquisition unit 13. Also, the control unit 101 receives start information indicating that the fluorescent dye is injected into the living organism S from the input unit 17 and instructs the analysis unit 103 to perform an operation when a predetermined time has elapsed from the input of the start information. The predetermined time is preset as any time of one minute or more.

The image processing unit 102 includes an image processing circuit for adjusting the luminance of the fluorescence image including the image of the background and the image of the fluorescence. More specifically, if fluorescence image data is received from the image acquisition unit 13, the image processing unit 102 acquires the fluorescence image by executing black level adjustment and gain adjustment on the fluorescence image data. The image processing unit 102 outputs the fluorescence image obtained by image processing to the analysis unit 103, the display unit 15, and the storage unit 16.

Figure 3:
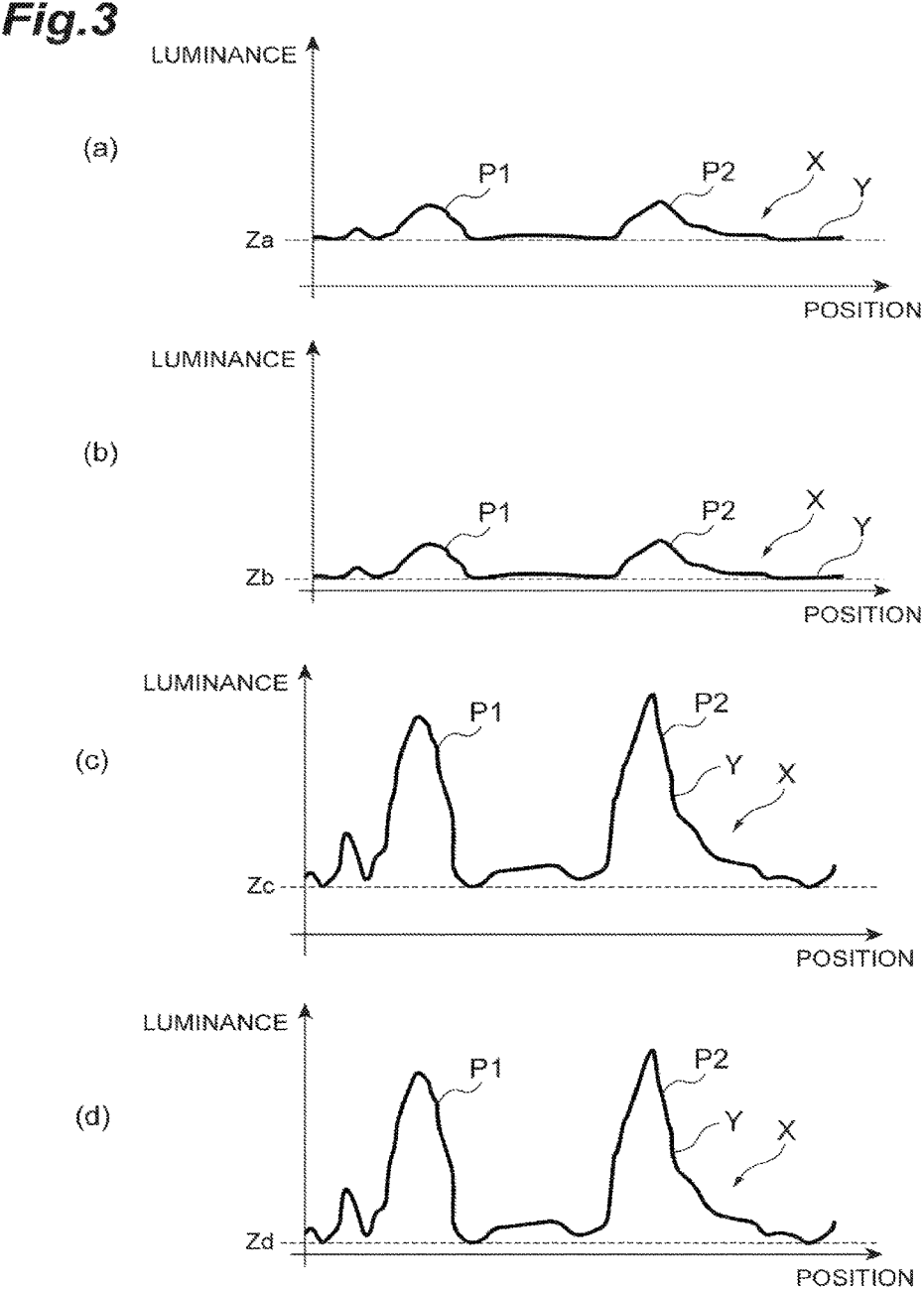
FIG. 3 is a diagram illustrating image processing in an image processing unit, wherein (a) illustrates a luminance distribution of a fluorescence image before image processing, (b) illustrates a luminance distribution of a fluorescence image after black level adjustment, (c) illustrates a luminance distribution of a fluorescence image after gain adjustment, and (d) illustrates a luminance distribution of a fluorescence image after second black level adjustment.

FIG. 3 is a diagram illustrating image processing in the image processing unit 102. In the example of FIG. 3, the horizontal axis represents a position, the vertical axis represents luminance, and a luminance distribution X of the fluorescence image is illustrated on the basis of a luminance distribution of the fluorescence image and a luminance level of the image of the background. FIG. 3(a) illustrates a luminance distribution of a fluorescence image before image processing. In the example of FIG. 3(a), in the luminance distribution Y of the fluorescence image, two luminance peaks P1 and P2 are present at positions separated from each other. Also, the luminance level of the image of the background becomes Za at any position.

FIG. 3(b) illustrates a luminance distribution of a fluorescence image after black level adjustment. In the black level adjustment, the level of the image of the background is reduced while the luminance of the fluorescence image is maintained. In the normal black level adjustment, the luminance level of the image of the background is adjusted to 0. However, in this image processing, the luminance level of the image of the background remains below Za at Zb. FIG. 3(c) illustrates a luminance distribution of a fluorescence image after gain adjustment. Here, the luminance of the image of the fluorescence is mainly emphasized. Here, in the gain adjustment, the luminance level of the image of the background is also increased above Za to Zc. FIG. 3(d) illustrates a luminance distribution of a fluorescence image after the second black level adjustment. The luminance level of the image of the background emphasized in the gain adjustment is reduced to about Zd, which is equivalent to Zb, by black level re-adjustment. Thereby, the luminance of the image of the fluorescence increases with respect to the level Zd of the image of the background.

The analysis unit 130 includes an analysis processing circuit which specifies a linear fluorescence pattern appearing in the fluorescence image. When an instruction of execution of an operation is received from the control unit 101, the analysis unit 103 executes image analysis of the fluorescence image after image processing from the image processing unit 102. The timing at which the analysis unit 103 receives an instruction from the control unit 101 is when one minute or more has elapsed from the input of start information indicating that the fluorescent dye is injected into the observation object K to the control unit 101. Therefore, the fluorescent dye is introduced into the observation object K along with the passage of the time and, after a pattern corresponding to lymphedema first appears in the fluorescence image, the linear fluorescence pattern extending from the pattern appears.

The analysis unit 130 specifies a shape, a position, a direction, and the like of a lymphatic linear fluorescence pattern in the fluorescence image by the image analysis. The analysis unit 103 generates specification information indicating information thereof and adds the specification information to the fluorescence image to cause the fluorescence image to be displayed on the display unit 15 and cause the fluorescence image to be stored in the storage unit 16. The image analysis method used in the analysis unit 103 is not particularly limited, but it is possible to use, for example, a technique of recognizing a pattern of a time-variant luminance distribution, a technique of acquiring a difference image among a plurality of continuously acquired images, etc. Also, the control circuit of the control unit 101, the image processing circuit of the image processing unit 102, and the analysis processing circuit of the analysis unit 103 may be constituted of a single processor or a plurality of processors.

Next, a fluorescence observation method using the above-described fluorescence observation device 1 will be described.

Figure 4:
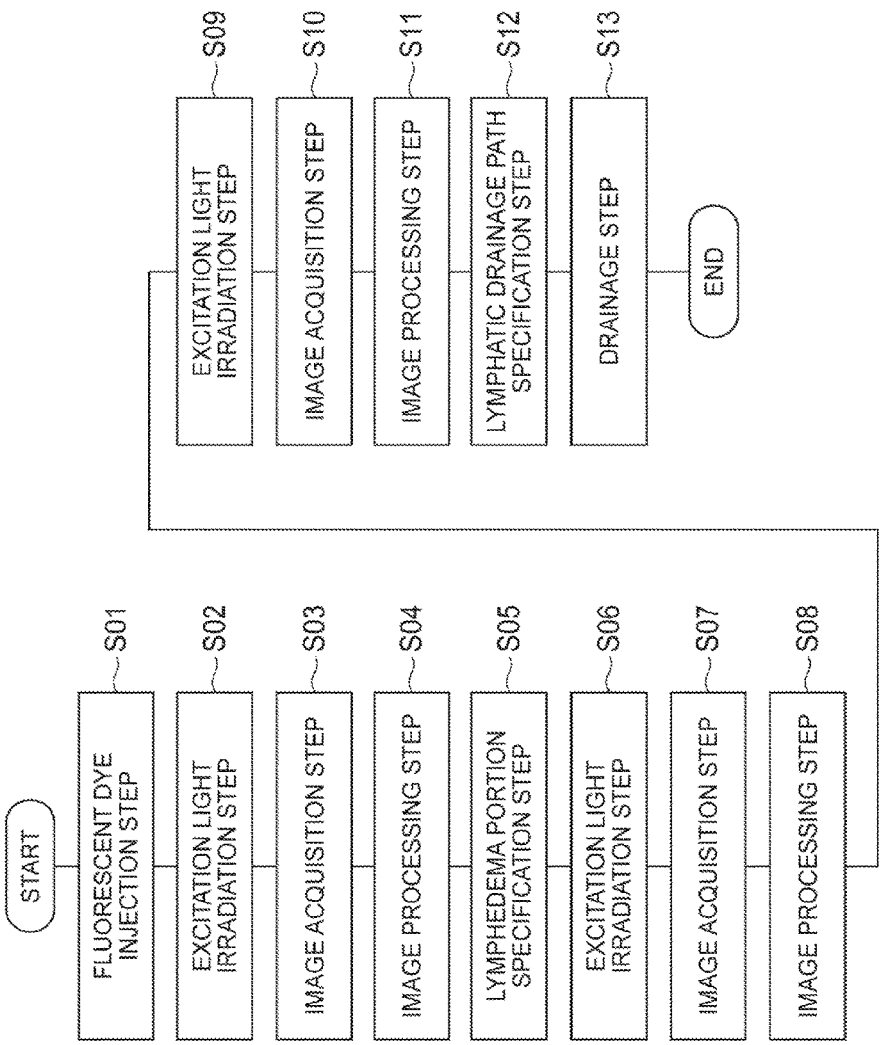
FIG. 4 is a flowchart illustrating an example of a fluorescence observation method using the fluorescence observation device illustrated in FIG. 1.

FIG. 4 is a flowchart illustrating an example of the fluorescence observation method. As illustrated in FIG. 4, the fluorescence observation method includes a fluorescent dye injection step (step S01), an excitation light irradiation step (step S02), an image acquisition step (step S03), an image processing step (step S04), and a lymphedema portion specification step (step S05) as steps of specifying the observation object K. Also, the fluorescence observation method includes an excitation light irradiation step (step S06), an image acquisition step (step S07), and an image processing step (step S08) as the steps of acquiring a fluorescence image in the step in which no lymphatic drainage path appears.

Also, the fluorescence observation method includes an excitation light irradiation step (step S9), an image acquisition step (step S10), and an image processing step (step S11) as the step of acquiring the fluorescence image in the step in which the lymphatic drainage path has appeared. Further, the fluorescence observation method includes a lymphatic drainage path specification step of specifying the lymphatic drainage path (step S12) and a drainage step of performing treatment based on the specified lymphatic drainage path (step S13).

In the fluorescent dye injection step (step S01), the fluorescent dye is injected into the living organism S. For example, a syringe is used in the injection of the fluorescent dye. In general, lymphedema occurs in limbs in many cases. In this case, an injection portion of the fluorescent dye is designated on the skin surface of a hand or a foot. When the injection of the fluorescent dye has been completed, the input unit 17 inputs the fact that the injection of the fluorescent dye has been completed to the fluorescence observation device 1. The injected fluorescent dye is introduced into a lymphatic vessel from the inside of the skin and gradually spreads to a portion in which lymphedema occurs according to a flow of lymph. Also, it is preferable to protect the injection portion using a tape, an adhesive plaster, or the like after the injection of the fluorescent dye. Thereby, it is possible to prevent an observation region from being contaminated due to the attachment of the fluorescent dye to another portion or an observer.

After the fluorescent dye is injected into the living organism S, the observation object K is first specified on the basis of the fluorescence image of the living organism S. In the excitation light irradiation step (step S02), the living organism S is irradiated with excitation light. The fluorescent dye injected into the living organism S is excited by the irradiation with the excitation light and fluorescent light is generated from the fluorescent dye introduced into the lymphatic vessel. In the image acquisition step (step S03), fluorescence image data is acquired by imaging the fluorescent light generated by the irradiation with the excitation light along with a part of the background light together.

In the image processing step (step S04), luminance adjustment of the fluorescence image data is performed and a fluorescence image (a first fluorescence image) including an image of a background of the living organism S and an image of fluorescence is acquired. In the luminance adjustment, a luminance level of the image of the fluorescence is increased while the luminance level of the image of the background is maintained at a low level by the black level adjustment and the gain adjustment (see FIG. 3). The fluorescence image obtained in the image processing step (step S04) is stored in the storage unit (a storage) 16 and displayed on the display unit (a display) 15.

In the lymphedema portion specification step (step S05), the portion of the lymphedema in the living organism S is specified as the observation object K on the basis of the fluorescence image acquired in the image processing step (step S04). Here, the observer specifies the portion of the lymphedema on the basis of the fluorescence image displayed on the display unit 15. The observer may designate the portion of the lymphedema using the input unit 17 such as, for example, a mouse.

After the observation object K is specified, the fluorescence image of the observation object K is acquired in the step before the fluorescent dye is circulated in the lymphatic drainage path. In the excitation light irradiation step (step S6), the observation object K specified in the lymphedema portion specification step (step S05) is irradiated with the excitation light. According to the irradiation with the excitation light, the fluorescent dye in the observation object K is excited and fluorescent light is generated. Next, in the image acquisition step (step S07), a part of the background light from the observation object K and fluorescent light from the fluorescent dye in the observation object K are imaged together and fluorescence image data is acquired.

In the image processing step (step S08), the luminance adjustment of the fluorescence image data acquired in the image acquisition step (step S07) is performed and a fluorescence image (a third fluorescence image) including an image of a background of the observation object K and an image of fluorescence is acquired. In this luminance adjustment, as in the image processing step (step S04), the luminance level of the image of the fluorescence is increased while the luminance level of the image of the background is maintained low according to black level adjustment and gain adjustment (see FIG. 3). Thereby, a fluorescence image in which there is no fluorescence pattern corresponding to a lymphatic drainage path is acquired. The fluorescence image processed in the image processing step (step S08) is stored in the storage unit 16 and displayed on the display unit 15. Also, if the luminance adjustment is sufficient in the image processing step (step S04) before the specification of the lymphedema portion, it is only necessary to perform the luminance adjustment of the image processing step of step S08 in the same condition.

Further, the fluorescence image of the observation object K is acquired in the step in which the fluorescent dye is circulated in the lymphatic drainage path. In the excitation light irradiation step (step S09), the observation object K is irradiated with the excitation light. According to the irradiation with the excitation light, the fluorescent dye in the observation object K is excited and fluorescent fight is generated. In the image acquisition step (step S10), the background light from the observation object K and the fluorescent light from the fluorescent dye in the observation object K are imaged together and fluorescence image data is acquired.

In the image processing step (step S11), the luminance adjustment of the fluorescence image data acquired in the image acquisition step (step S10) is performed. In the luminance adjustment, as in the image processing step (step S04 and step S08), the luminance level of the image of the fluorescence is increased while the luminance level of the image of the background is maintained low according to black level adjustment and gain adjustment (see FIG. 3). Thereby, a fluorescence image (a second fluorescence image) including a fluorescence pattern corresponding to the lymphatic drainage path is acquired. Also, if luminance adjustment is sufficient in the image processing step (step 04) as in the image processing step (step S08), it is only necessary to perform the luminance adjustment of the image processing step of step S10 in the same condition. The fluorescence image obtained in the image processing step (step S11) is stored in the storage unit 16 and displayed on the display unit 15.

The excitation light irradiation step (step S09) and the image acquisition step (step S10) are performed after a predetermined time of one minute or more has elapsed from the completion of injection of the fluorescent dye in the fluorescent dye injection step (step S01). According to the passage of the predetermined time, the image acquisition step (step S10) is performed in a state in which the fluorescent dye is sufficiently introduced into a portion in which lymphedema occurs and the fluorescent dye is also sufficiently circulated in the lymphatic drainage path extending from the lymphedema to the normal lymphatic system. Therefore, the lymphatic drainage path appears as the fluorescence pattern linearly extending from the lymphedema in the obtained fluorescence image of the observation object K. Also, after the injection of the fluorescent dye in the fluorescent dye injection step, the massage or the like may be performed on the portion in which the lymphedema occurs to sufficiently introduce the fluorescent dye.

In the lymphatic drainage path specification step (step S12), a shape, a position, and a direction of the lymphatic drainage path are specified on the basis of the linear fluorescence pattern appearing in the fluorescence image. The specification of the lymphatic drainage path is performed by image analysis of the fluorescence image and the fluorescence image including specification information is stored in the fluorescence observation device 1. The fluorescence image after image processing is displayed on the display unit 15 in real time along with the specification information. At this time, because the image of the background is included in the fluorescence image, an indicator material such as a finger or a pen is close to the observation object K and a positional relationship between the actual lymphedema and the indicator material appears in the fluorescence image displayed on the display unit 15. Therefore, it is possible to easily visually recognize a shape, a position, and a direction of the lymphatic drainage path.

Also, in the lymphatic drainage path specification step (step S12), the observer may specify the linear fluorescence pattern appearing in the fluorescence image on the basis of the image of the observation object K displayed on the display unit 15. In this case, for example, each of the fluorescence image (the third fluorescence image) acquired in the image processing step (step S08) and the fluorescence image (the second fluorescence image) acquired in the image processing step (step S11) is displayed on the display unit 15 and the observer specifies the linear fluorescence pattern appearing in the fluorescence image by comparing the two images. Also, if the fluorescence image can be acquired by the image acquisition unit 13 in time series, the observer may specify the linear fluorescence pattern appearing in the fluorescence image on the basis of an extending direction of the fluorescence image by displaying a moving image thereof on the display unit 15.

In the drainage step, the vicinity of the lymphedema is massaged. In the drainage step, the living organism S is massaged from the lymphedema to the lymphatic drainage path on the basis of the shape, the position, and the direction of the lymphatic drainage path specified in the lymphatic drainage path specification step. Thereby, lymph in which a flow deteriorates in the vicinity of the lymphedema is drained to the normal lymphatic system via the lymphatic drainage path.

As described above, in the fluorescence observation device 1 and the fluorescence observation method, the observation object K which is lymphedema is specified on the basis of a fluorescence image of the living organism S obtained by irradiating the living organism S into which a fluorescent dye is injected with excitation light. Next, a linear fluorescence pattern appearing in the fluorescence image is specified on the basis of the fluorescence image of the observation object K obtained by irradiating the specified observation object K with the excitation light. Specifically, a linear fluorescence pattern appearing in the fluorescence image is specified by comparing a fluorescence image before the fluorescent dye is circulated in the lymphatic drainage path with a fluorescence image after the fluorescent dye is circulated in the lymphatic drainage path. The linear fluorescence pattern is a fluorescence pattern indicating the lymphatic drainage path along which lymph is drained from a portion in which lymphedema occurs to the normal lymphatic system. Therefore, it is possible to precisely recognize the lymphatic drainage path by specifying the linear fluorescence pattern.

Also, in the fluorescence observation device 1 and the fluorescence observation method, the acquisition of the fluorescence image of the observation object K is performed when at least one minutes has elapsed from the injection of the fluorescent dye into the living organism S. The analysis unit 103 specifies the linear fluorescence pattern when one minute or more has elapsed from the injection of the fluorescent dye into the living organism S. Thereby, it is possible to recognize the lymphatic drainage path more precisely because the linear fluorescence pattern in the fluorescence image appears clearly.

Also, in the fluorescence observation device 1 and the fluorescence observation method, fluorescent light from the living organism S and a part of background light are input to the image acquisition unit 13 by the light filter 12. Thereby, it is possible to capture an image of a background including an image of an indicator material such as a finger or a pen and an image of fluorescence together. The lymphatic drainage path is easily recognized on the basis of the specification of the linear fluorescence pattern when the indicator material is designated as a reference.

Further, in the fluorescence observation device 1 and the fluorescence observation method, the image processing unit 102 adjusts luminance of the image of the background and the image of the fluorescence in the fluorescence image. Thereby, the luminance of the linear fluorescence pattern in the fluorescence image is emphasized and the recognition of the lymphatic drainage path is further facilitated.

Figure 5:
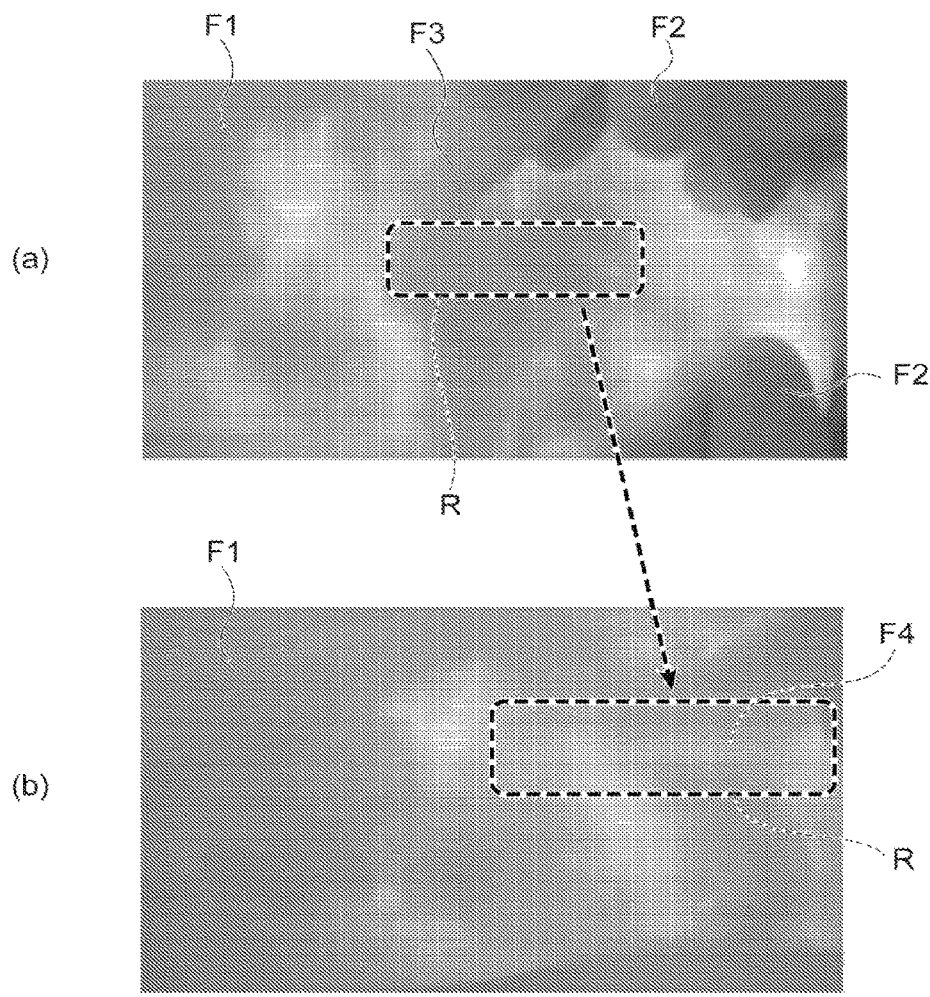
FIG. 5 is a diagram illustrating an observation example of lymphedema, wherein (a) illustrates a fluorescence image before linear fluorescence pattern appearance and (b) illustrates a fluorescence image after the linear fluorescence pattern appearance.

FIG. 5 is a diagram illustrating an observation example of lymphedema. A fluorescence image illustrated in FIG. 5(a) is a fluorescence image before linear fluorescence pattern appearance. Because the fluorescence image is an image before one minute has elapsed from the injection of the fluorescent dye into the living organism S and is the fluorescence image before the fluorescent dye is circulated in the lymphatic drainage path, only a pattern F1 corresponding to the lymphedema appears. Also, a shadow F2 of an upper/lower right side of the fluorescence image is a shadow in which fingers of the observer appear as the image of the background. Here, a shadow F3 of a pen held at a fingertip by the observer also appears. A fluorescence image illustrated in FIG. 5(b) is a fluorescence image after the linear fluorescence pattern appearance. Because this fluorescence image is an image after one minute or more has elapsed from the injection of the fluorescent dye into the living organism S and is a fluorescence image after the fluorescent dye is circulated in the lymphatic drainage path, a linear fluorescence pattern F4 extending from the pattern F1 appears in a region R indicated by a dotted line in FIG. 5(b). Therefore, it can be seen by comparing FIG. 5(a) and FIG. 5(b) that the linear fluorescence pattern which is a fluorescence pattern corresponding to the lymphatic drainage path can be specified.

The present invention is not limited to the above-described embodiment. For example, an example in which the light filter 12 which transmits fluorescent light from the living organism S and the observation object K and a part of background light is shown as a light control means in the above-described embodiment, but the light control means may be constituted of an optical element such as a dichroic mirror which reflects the fluorescent light from the living organism S and the observation object K and the part of background light and an optical system which guides the reflected light to the image acquisition unit 13. Also, an example in which light of a fluorescent lamp serves as the background light is shown in the above-described embodiment, but the background light may include reflected light or the like obtained by reflecting natural light or excitation light by the living organism S and the observation object K in addition to light of the fluorescent lamp.

Also, each of an image (a background image) of only an image of a background of the living organism S or the observation object K and a fluorescence image including the image of the background and the image of the fluorescence of the living organism S or the observation object K may be acquired by turning light irradiation ON/OFF by the light irradiation unit 11. In this case, the image processing unit 102 can acquire a difference image between the background image and the fluorescence image and acquire the fluorescence image including the image of the background and the image of the fluorescence by superimposing the difference image on the background image.

Also, in the fluorescence observation device 1, the light irradiation unit 11 and the image acquisition unit 13 may be configured integrally or separately.

REFERENCE SIGNS LIST

1 Fluorescence observation device
11 Light irradiation unit (light irradiation means)
12 Light filter (light control means)
13 Image acquisition unit (image acquisition means)
102 Image processing unit (image processing means)
103 Analysis unit (analysis means)
F4 Linear fluorescence pattern
K Observation object

The invention claimed is:

1. A method for massaging a living organism, the method comprising:
   injecting a fluorescent dye into the living organism;
   irradiating the living organism with excitation light including a wavelength for exciting the fluorescent dye using a light source;
   capturing a first fluorescent image generated from the fluorescent dye introduced into a lymphatic vessel by the irradiation with the excitation light using an image sensor, before the fluorescent dye is circulated in a lymphatic drainage path;
   capturing a second fluorescent image generated from the fluorescent dye introduced into the lymphatic vessel by the irradiation with the excitation light using the image sensor, after the fluorescent dye is circulated in the lymphatic drainage path;
   displaying the first and second fluorescent images on a display to specify the lymphatic drainage path; and
   massaging the living organism to the lymphatic drainage path.

2. The method according to claim 1,
   wherein the displaying separately displays the first and second fluorescent images on the display.

3. The method according to claim 1,
   wherein the displaying displays a movie including the first and second fluorescent images.

4. The method according to claim 1, further comprising:
   protecting an injection portion using a tape or an adhesive plaster after the injection of the fluorescent dye.

5. The method according to claim 1, further comprising:
   the first and second fluorescent images having a fluorescence pattern corresponding to a lymphedema portion; and
   displaying the first and second fluorescent images to specify the lymphedema portion.

6. The method according to claim 1, further comprising:
   adjusting an illumination level of the first and second fluorescent images.

7. The method according to claim 6,
   wherein the adjusting adjusts a black level and a gain to increase a luminance level of the first and second fluorescent images while a luminance level of a background image is maintained at a lower level.

* * * * *